(12) United States Patent
Matz et al.

(10) Patent No.: US 8,008,314 B2
(45) Date of Patent: Aug. 30, 2011

(54) METHOD OF RECOVERING CYANOPYRIDINES

(75) Inventors: Michael J. Matz, Saginaw, MI (US); Chen Wang, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 146 days.

(21) Appl. No.: 11/835,266

(22) Filed: Aug. 7, 2007

(65) Prior Publication Data

US 2008/0039632 A1    Feb. 14, 2008

Related U.S. Application Data

(60) Provisional application No. 60/821,779, filed on Aug. 8, 2006.

(51) Int. Cl.
*A61K 31/435* (2006.01)

(52) U.S. Cl. ...................................... 514/277
(58) Field of Classification Search .................. 514/277; 546/286

See application file for complete search history.

(56) References Cited

U.S. PATENT DOCUMENTS

| | | | |
|---|---|---|---|
| 3,689,491 A | 9/1972 | Suvorov et al. | |
| 4,341,907 A | 7/1982 | Zelonka | |
| 4,603,207 A | 7/1986 | DiCosimo et al. | |
| 4,730,043 A | 3/1988 | van der Stoel | |
| 4,810,794 A | 3/1989 | Shimizu et al. | |
| 5,384,404 A | 1/1995 | Lee | |
| 5,698,701 A * | 12/1997 | Sembaev et al. | 546/286 |
| 5,719,045 A | 2/1998 | Heveling et al. | |
| 5,895,635 A | 4/1999 | Brazdil, Jr. et al. | |

FOREIGN PATENT DOCUMENTS

| | | |
|---|---|---|
| EP | 1179359 | 2/2002 |
| GB | 790937 | 2/1958 |
| JP | 63010753 | 1/1988 |
| JP | 9 136876 | 5/1997 |

OTHER PUBLICATIONS

C. H. McAteer and E. F. V. Scriven Heterocyclic Synthesis, Wiley-VCH 2001, 1st Ed, p. 275.*
"Pyridine and Pyridine Derivatives" Kirk-Othmer Concise Encyclopedia of Chemical Technology, Jan. 11, 2001, Wiley-Interscience, 4th Ed, vol. 20, p. 1-33.*
International Searching Authority, "International Search Report," for PCT/US2007/075390, Jan. 25, 2008, 4 pages.
International Searching Authority, "Written Opinion of the International Searching Authority," for PCT/US2007/075390, Jan. 25, 2008, 5 pages.
Database WPI Week 1997 Derwent Publications Ltd., London, GB, "XP-002464537," for PCT/US2007/075390, Jan. 25, 2008, 1 page.

* cited by examiner

*Primary Examiner* — Rita Desai
*Assistant Examiner* — John Mabry
(74) *Attorney, Agent, or Firm* — Craig E. Mixan; Baker & Daniels LLP

(57) ABSTRACT

Hydrolysis of cyanopyridine may be reduced by use of picoline as a predominately non-aqueous quench fluid. The picoline quench fluid may also be a reactant in the manufacture of cyanopyridine.

6 Claims, No Drawings

METHOD OF RECOVERING CYANOPYRIDINES

CLAIM FOR PRIORITY

This application claims the benefit of the filing date of U.S. Provisional Patent Application Ser. No. 60/821,779, filed Aug. 8, 2006, entitled "A Method of Making Cyanopyridines", the disclosure of which is expressly incorporated by reference.

BACKGROUND OF THE INVENTION

The present invention relates to the preparation of cyanopyridines. Cyanopyridines are useful as intermediates in the manufacture of useful compounds. In U.S. Pat. No. 4,341,907, cyanopyridine serves a catalytic role. In U.S. Pat. No. 5,719,045, the preparation of cyanopyridine by ammoxidation from picoline (also known as methylpyridine) is disclosed. Cyanopyridines also find application as a building block for the preparation of other compositions, including crop protection chemicals such as the systemic broadleaf herbicides picloram (4-amino-3,5,6-trichloro-2-pyridine carboxylic acid) and aminopyralid (4-amino-3,6-dichloro-2-pyridine carboxylic acid).

In the production of cyanopyridine from picoline, aqueous quench fluids provide a convenient means to quench gaseous reaction mixtures containing cyanopyridine reaction product. The use of aqueous quench fluids, however, generates hydrolysis by-products. The present invention reduces hydrolysis by-products.

The preparation of substituted heterocyclic compounds is often conducted at elevated temperatures with gaseous reactants over a solid catalyst. Similarly, removal of substituents from heterocyclic compounds is also often conducted at elevated temperatures with gaseous reactants over solid catalysts. Typical of reactions that remove substituents from heterocyclic compounds is that disclosed in U.S. Pat. No. 3,689,491 concerning the oxidation of 3-picoline (3-methylpyridine or β-picoline) over vanadium pentoxide/titanium dioxide catalyst to produce pyridine. The reaction is said to be operated between 300° C. and 380° C. resulting in gaseous reaction product at that temperature. Gaseous reaction product exiting the reactor is quenched with cold water in a scrubber.

UK 790,937 describes the recovery of cyanopyridines from ammoxidation reactions involving picolines with ammonia and oxygen. A recycle of water including the water soluble reaction products is used to quench the gaseous reaction product containing cyanopyridine as it exits from the reactor. The cyanopyridine is subsequently separated from the quench water by cooling the water prior to recycle to the quencher. The recycled quench liquid includes by-products nicotinamide, cyanide, and $CO_2$.

U.S. Pat. No. 4,810,794 discloses absorbing gaseous reaction product including pyridine in water.

Cyanopyridines are manufactured by ammoxidation of picolines, as reactor feed. Ammoxidation reactions operate in temperature ranges from 300° C. to 450° C. Oxygen and ammonia in the presence of catalysts react with picolines to form cyanopyridines at high reaction temperatures. As may be expected, at lower temperatures reactions may be slowed to an uneconomical rate whereas as temperatures elevate the reaction generates increasing amounts of unwanted by-products. An economical operating temperature will balance reaction rate with desired reaction products.

For a typical aqueous quench in a picoline ammoxidation reaction, the gaseous reaction products are quenched from the reaction temperature to a temperature convenient for work up of reaction products, such as 50° C., in the quench operation. The aqueous quench fluid is fed to the quench operation at a sufficiently lower temperature to cool the reaction products to a temperature convenient for work up. As necessary, temperature adjustment of aqueous quench fluid is provided.

Typically, an organic extraction fluid, such as benzene, is useful to remove the cyanopyridine reaction product into the organic phase. The aqueous extraction fluid is recycled to the aqueous quench operation and added to necessary make up water. The organic phase benzene and cyanopyridine stream may be separated by distillation followed by work-up and purification of the product cyanopyridine. The organic extractant may be returned to the extraction step.

Hydrolysis of cyanopyridines can lead to pyridinecarboxamide (also known as picolinamide). It is thought that by-products such as pyridinecarboxamide result from hydrolysis of the desired cyanopyridine, a nitrile, in the presence of water and ammonia in the quench liquid. It would be desirable to recover cyanopyridine reaction products without generating hydrolysis by-products. Hydrolysis of pyridinecarboxamide, a hydrolysis product of cyanopyridine, can further lead to pyridine-2-carboxylic acid formation.

SUMMARY OF THE INVENTION

The invention relates to the quench of hot, gaseous reaction product containing cyanopyridine from the ammoxidation of picoline by use of a predominately non-aqueous quench fluid containing picoline.

DEFINITIONS

Ammoxidation is defined as the chemical process in which mixtures of organic material, in the presence of ammonia, oxygen and a catalyst, at elevated temperature, is converted to a cyano containing product.

Cyanopyridines are defined as the group of compounds that are at least one cyano derivative of pyridines. Cyanopyridines have many other common names including pyridyl nitriles, pyridinecarbonitriles, picolinic acid nitrites or pyridine carbonitriles.

Picolines are defined as the group of compounds that include at least one methyl derivative of pyridine. Picolines are also commonly referred to as methylpyridines.

Predominantly non-aqueous is defined as predominantly without water including majority without water.

DETAILED DESCRIPTION

By quenching gaseous reaction product including cyanopyridine with picoline, the loss of cyanopyridine to hydrolyzed by-products may be materially reduced and therefore the isolated yield of cyanopyridine may be materially increased.

Embodiments

The production of cyanopyridines involves the quench of gaseous reaction product using picolines as the predominately non-aqueous quench fluid. The picoline quench operation may be structured as follows. Gaseous reaction product may be contacted with quench fluid within a quenching system. The quenching system may include spraying quenching fluid to contact the gaseous reaction product using nozzles, weir, or falling film heat exchangers, or a separate chamber or tower having a spray system. The chamber or tower may be packed to increase surface area to increase operational efficiency.

The gaseous reaction product may exit the reactor within the approximate range of about 5,000 lbs/hr to about 15,000 lbs/hr, including approximately the rate of 10,850 lbs/hr. Predominately non-aqueous quench fluid may be provided within the approximate range of about 5,000 lbs/hr to about 15,000 bs/hr, including approximately the rate of 10,000 lb/hr. The ratio of gaseous reaction product to predominately non-aqueous quench fluid may be within the approximate range of about 1:3 to about 3:1, including approximately 1:1.

In one embodiment, the gaseous reaction product is quenched from the reaction temperature to a temperature convenient for work up of reaction products such as 70° C. in the quench operation. In this embodiment gaseous reaction product enters a packed tower having a distributor or spray system which provides predominantly non-aqueous quench fluid such as picoline. The gaseous reaction product is concurrent with the quench when exiting the packed tower and when entering a falling film condenser.

Within the condenser, picoline quench fluid absorbs cyanopyridine from the gaseous reaction product. The picoline quench fluid including cyanopyridine from the gaseous reaction product forms or remains in a liquid phase. The liquid phase may travel down the falling film condenser and may collect in a knock out pot. The liquid phase may be returned to the packed tower as quench fluid.

Vapor exiting the falling film condenser may also enter the knock out pot. The vapor may continue on as cycle gas back to the reactor, purge gas, or other further isolation processes. Picoline quench fluid may also supplement picoline reactor feed.

The liquid phase containing picoline and cyanopyridine may pass through the packed tower. The liquid phase containing picoline and cyanopyridine may or may not have passed through the falling film condenser and knockout pot. Picoline quench fluid may eliminate the need to perform an organic phase extraction (e.g. benzene) as utilized in an aqueous quench.

Cyanopyridine may be separated from picoline by distillation. The liquid phase, which may contain cyanopyridine, picoline, lighter materials and heavier materials, may be distilled to separate picoline and lighter materials from cyanopyridine and heavier materials. The lighter materials may include water, pyridines and light organics. The heavier materials may include pyridinecarboxamides. The portion including cyanopyridine and heavier materials may be further separated for additional isolation of cyanopyridine using a tower, a condenser and a kettle reboiler.

EXAMPLES

Example 1

A batch hydrolysis was designed to simulate the quench of gaseous reaction product from the preparation of 2-cyanopyridine prepared from 2-picoline reactor feed in the presence of air and ammonia over a catalyst. To a 100 mL glass tube reactor, 0.5 grams of 2-cyanopyridine, a magnetic stir bar, and 20 mL of an ammonia solution were added per Table 1. The tube was capped and heated at the temperatures and for the contact times indicated in Table 1. After each interval, the tube reactor was transferred to be cooled with a water bath and the tube's cap opened. After a gas chromatography sample of 2 μL of the solution was taken, the tube was recapped and heated for another interval of time.

The simulated aqueous quench fluid included ammonia representing unreacted ammonia. The samples were analyzed for remaining 2-cyanopyridine. The balance of the remaining 2-cyanopyridine is viewed as theoretical hydrolysis of 2-cyanopyridine to the corresponding pyridine-2-carboxamide (2-picolinamide). Under these conditions, hydrolysis at reaction times longer than 4 hours leads to significant amounts of pyridine-2-carboxylic acid.

TABLE 1

Quench Fluid - aqueous

| Temperature of Quench Fluid - ° C. | NH$_3$ content % wt | % of original 2-cyanopyridine remaining | | | % converted to pyridine-2-carboxamide | | |
|---|---|---|---|---|---|---|---|
| | | 2 hours | 4 hours | 6 hours | 2 hours | 4 hours | 6 hours |
| 30 | 2 | 96 | 92 | | 4 | 8 | |
| 45 | 2 | 85 | 74 | 63 | 15 | 16 | 37 |
| 60 | 2 | 65 | 40 | | 35 | 60 | |
| 75 | 2 | 47 | 26 | 18 | 53 | 74 | 82 |
| 75 | 1 | 54 | 34 | 26 | 46 | 66 | 74 |
| 75 | 0.5 | 63 | 46 | 40 | 37 | 54 | 60 |
| 75 | 0.1 | 84 | 71 | 62 | 16 | 29 | 38 |

Table 1 demonstrates that the desired cyanopyridine product hydrolyzes in aqueous quench fluid to pyridinecarboxamide.

Example 2

The batch hydrolysis simulation of Example 1 was repeated with a predominately non-aqueous quench fluid comprising 2-cyanopyridine in 2-picoline solution, water and ammonia in the respective weight percents indicated in Table 2. To a 100 mL glass tube reactor were added 6.25% 2-cyanopyridine in 2-picoline solution. Under these conditions, the predominately non-aqueous quench fluid was stirred at the temperatures for the contact times indicated in Table 2 below. Samples were analyzed at the indicated intervals for the hydrolyzed by-product pyridinecarboxamide.

TABLE 2

Quench Fluid - 2-picoline

| Temperature of Quench Fluid - ° C. | H$_2$O content % wt | NH$_3$ content % wt | % converted to pyridinecarboxamide | | | |
|---|---|---|---|---|---|---|
| | | | 2 hours | 4 hours | 8 hours | 24 hours |
| 75 | 5 | 0.1 | 0 | 0 | 0 | 0 |
| 75 | 10 | 1 | .14 | .18 | .22 | .25 |
| 100 | 10 | 1 | .11 | .23 | .3 | .36 |
| 100 | 20 | 2 | .33 | .46 | .7 | 1.22 |

2-Cyanopyridine quenched in 2-picoline demonstrates a lower rate of hydrolysis to the undesired pyridine-2-carboxamide.

Examples 1 and 2 demonstrate that a reduction in water content in quench fluid leads to a lower rate of hydrolysis. Example 2 also demonstrates that a predominately non-aqueous quench fluid substantially minimizes pyridinecarboxamide formation and pyridinecarboxylic acid formation and substantially improves cyanopyridine isolation yield. Example 2 also demonstrates that a predominately non-aqueous quench fluid substantially minimizes hydrolysis while the quench fluid is at elevated temperatures compared to aqueous quench fluid.

The invention claimed is:

1. A method of quenching gaseous reaction mixtures, comprising the step of:
   supplying a reaction mixture that contains predominately 2-cyanopyridine;
   providing a quench fluid that contains predominately 2-picoline, and not more than 20% water; and
   contacting the reaction mixture with said predominately non-aqueous quench fluid.

2. The method of claim 1 wherein the only cyanopyridine in the reaction mixture is 2-cyanopyridine.

3. The method of claim 1 wherein said quench fluid minimizes hydrolysis of the 2-cyanopyridine as compared to quenching with a predominately aqueous quench fluid.

4. The method of claim 1, wherein said quench fluid includes not more than 10% water.

5. The method of claim 1, wherein said quench fluid includes not more than 5% water.

6. The method of claim 1, wherein said quench fluid includes at least 0.1% ammonia.

\* \* \* \* \*